United States Patent [19]

Laird et al.

[11] Patent Number: 4,484,481

[45] Date of Patent: Nov. 27, 1984

[54] GAS SAMPLING EXTRACTOR AND CONDITIONING ASSEMBLY

[75] Inventors: Daniel G. Laird; James C. Laird; Robert L. Tomlin, all of Waldron, Ark.

[73] Assignee: Sampling Technology, Inc., Waldron, Ark.

[21] Appl. No.: 430,844

[22] Filed: Sep. 30, 1982

[51] Int. Cl.³ .............................................. G01N 1/24
[52] U.S. Cl. .................................................. 73/863.12
[58] Field of Search ........... 73/863.11, 863.12, 863.21, 73/863.23, 863.24

[56] References Cited

U.S. PATENT DOCUMENTS

| 1,809,325 | 6/1931 | Austin et al. | 73/864.73 |
| 3,070,990 | 1/1963 | Krinov | 73/863.12 |
| 3,289,481 | 12/1966 | Barnes | 73/863.12 |
| 3,593,023 | 7/1971 | Dodson | 73/863.12 |
| 3,759,087 | 9/1973 | Iwao | 73/863.12 |
| 4,161,883 | 7/1979 | Laird et al. | 73/863.4 |
| 4,379,412 | 4/1983 | Wood | 73/863.4 |
| 4,383,694 | 5/1983 | Fontana | 277/228 |
| 4,386,534 | 6/1983 | Englund | 73/863.12 |

FOREIGN PATENT DOCUMENTS 2603948 9/1976 Fed. Rep. of Germany ... 73/863.23

Primary Examiner—S. Clement Swisher
Attorney, Agent, or Firm—Dennison, Meserole, Pollack & Scheiner

[57] ABSTRACT

A gas sampling extractor for extracting a stack gas sample for analysis. The gas sampling extractor includes a filter housing and an eductor in combination with gas conditioning apparatus for sampling and conditioning the emission pollutant content of a gaseous medium in a stack prior to introducing the sample gas to a measuring instrument for further analysis thereof.

28 Claims, 9 Drawing Figures

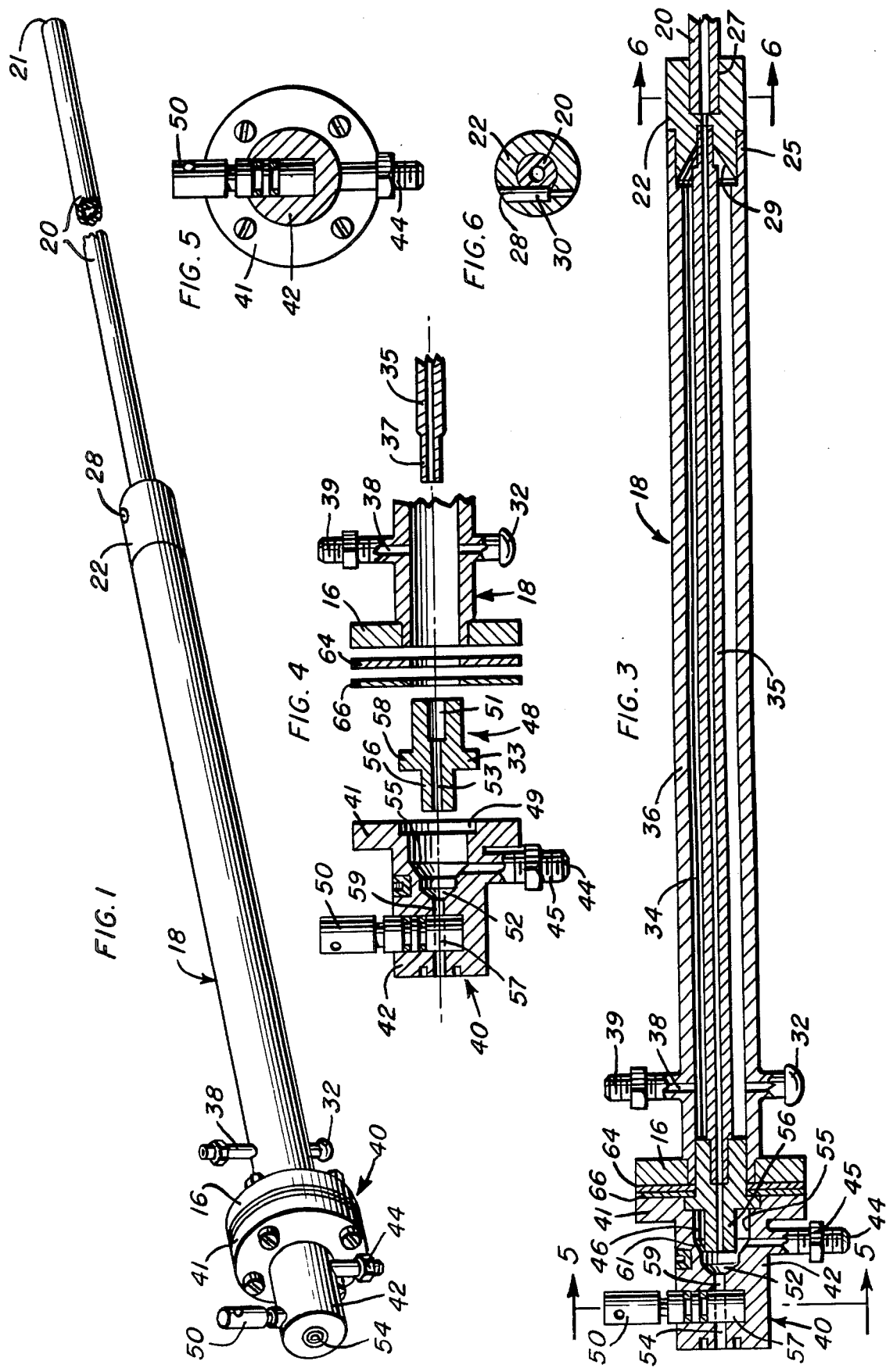

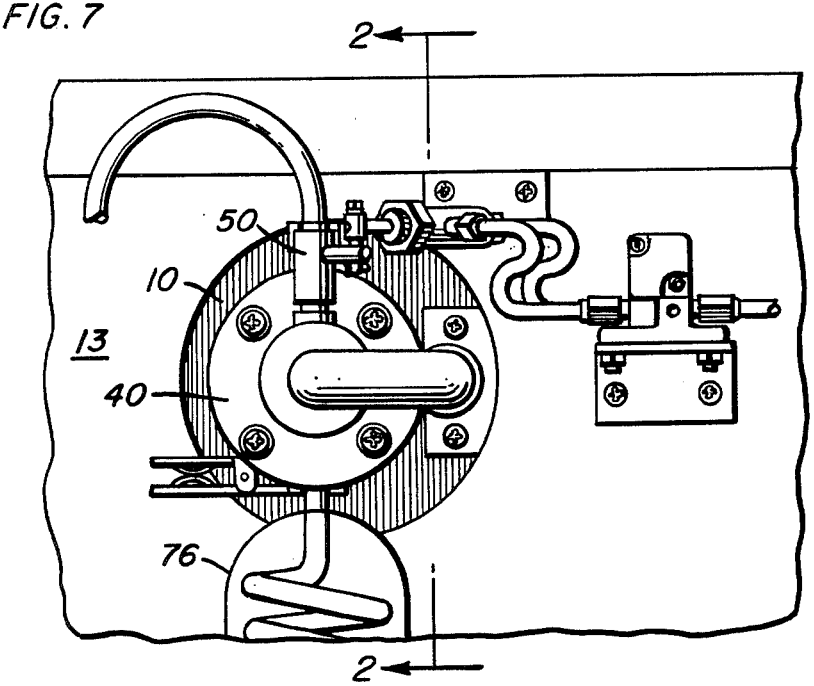
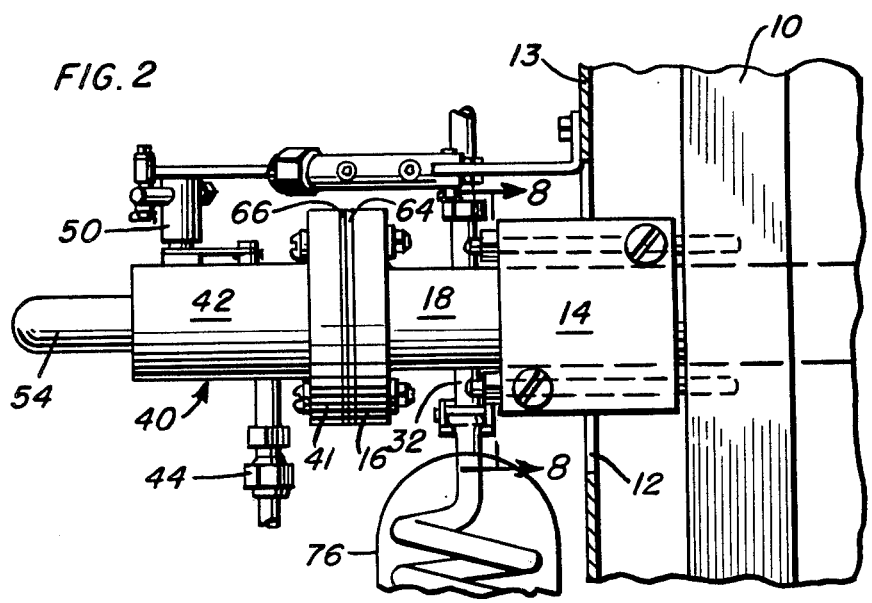
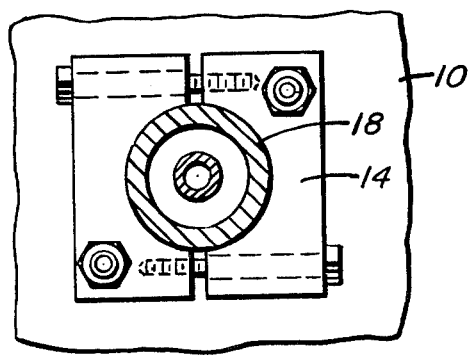

GAS SAMPLING EXTRACTOR AND CONDITIONING ASSEMBLY

BACKGROUND OF THE INVENTION

1. Field of the Invention

This invention relates to apparatus for measuring the particulate matter content in a gaseous medium; and, more particularly, to a gas sampling extractor and sample conditioning assembly for continuous monitoring of stack gases.

2. Description of the Prior Art

Environmental considerations necessitate the cleaning of exhaust gases which are the by-products of many industrial systems. Apparatus for measuring the particulate content and contaminants of gaseous media or exhaust gases are a significant component in many systems for monitoring and controlling particulate emissions.

Various types of apparatus have been developed for providing a treated gas sample to a gas analyzer, but none of the presently available commercial types of which we are aware provide truly representative samples of multi-component high temperature furnace or stack gases which frequently contain a high proportion of solids and generally substantial amounts of moisture, carbon dioxide or carbon monoxide and other undesirable contaminants.

Due to the sensitivity of the instrumentation required in the modern multi-component gas analyzers, it is necessary to remove substantial portions of the particulate matter entrained in the original gas sample without adversely affecting the gaseous components which are to be analyzed. Elimination of particulate matter is accomplished by filtering the gases from the solid matter in the gas stream. In addition the gas conduit lines conveying the gaseous sample from the source to the gas analyzer must be kept free of contaminants and matter which may cause accumulation resulting in blockage thereof while preserving the original gaseous nature of the sample either by heating the gas conduit lines to maintain all constituents of the sample at a temperature above their dew points throughout their transit of the line or, preferably, by conditioning the sample to remove corrosive aersols and water vapor therefrom.

SUMMARY OF THE INVENTION

A gas sampling extractor having a filter housing and an eductor in combination with gas conditioning apparatus is provided for sampling the emission pollutant content of a gaseous medium in a stack prior to introducing the sample gas to a measuring instrument for further analysis thereof.

In the present invention, the flanged elongate tubular filter housing includes a coaxial tubular probe assembly or portion, a coaxial tubular probe extension mounted on the end of the terminal end of the filter housing and having an open end in communication with a gaseous source such as a stack interior from which a gas sample is extracted. The filter housing and tubular probe extension may be made of a suitable synthetic polymer, ceramic or metallic material such as porous alumina ceramic, brass, bronze, stainless steel, copper and the like. The primary consideration in the selection of the material is that it be capable of withstanding the gaseous environment in which the extractor must function. The extracted sample is conducted into an inertial filter element having an inner spaced coaxially mounted concentric filter element fabricated in tubular form preferably of porous alumina ceramic material. The space between the inner wall surface of said assembly and the outer wall surface of said filter element defines a cell. The porosity of the filter element should be not less than about 5 microns. The tubular extension provides a path to conduct a gas sample from the gaseous source into the filter element. A filtered gas outlet port extends through the wall of the filter housing and into said cell. A gas calibration port may also extend into the cell if desired. A fluid operated eductor is fitted to the end of the filter housing opposite the terminal end portion. A filter housing mounting flange is provided adjacent the eductor body for mounting the extractor such as on the exterior of a stack wall. The fluid operated eductor assembly or portion includes a flanged ceramic or metallic eductor body, a chamber within said eductor body, a fluid inlet in communication with said chamber, an eductor jet defining a conduit for a stack sample to flow from the filter element into the eductor assembly, a blow back valve and eductor exhaust. The eductor assembly also includes an eductor venturi vent through which pressurized fluid fed into the eductor chamber from the fluid inlet passes selectively into an eductor vent outlet or exhaust. The blow back valve defines a passageway for fluid passing from the eductor chamber into the eductor vent outlet. When in a closed position, the valve reverses and directs the fluid entering the eductor body from the fluid inlet back through the eductor jet, the inertial filter assembly and into the stack thereby purging the filter element of entrained matter that may have accumulated on the inner surface walls of the filter element.

An eductor body flange sealably interconnects the eductor body assembly to the housing flange of the filter housing assembly. A flange sealing gasket and a sealing diaphragm define a compound seal and are positioned between the eductor body flange and the housing flange of filter housing assembly. In a preferred embodiment the flange gasket is made of a synthetic polymer such as polytetrafluoroethylene and the sealing diaphragm is a suitable flexible metallic diaphragm made of stainless steel, brass, copper and the like. It is of course appreciated that any suitable material may be utilized in the construction of the compound seal. In the event that fluid entering the eductor assembly should leak back across the ceramic seal sealing the eductor jet within the eductor assembly, the non-metallic gasket and metallic sealing diaphragm acts as a diversionary vent to atmosphere and precludes such fluid from entering the cell of the filter assembly housing and mixing with and thus contaminating the stack sample gas before it is extracted through the filtered sample gas outlet.

When pressurized fluid is directed into the eductor body a vacuum is established within the eductor body chamber thereby producing a flow of unfiltered sample gas into the inertial filter and simultaneously imparting momentum to entrained particles in the sample gas within the filter. A portion of the sample gas may be drawn off through the sample outlet port communicating with the filter wall. The filtered sample is transported to appropriate conditioning apparatus located exteriorly of the gaseous source. Thereafter the gas sample is treated by the conditioning apparatus to purge acid mists and water vapor from the sample after which the sample is routed to remotely located analytical instrumentation for further analysis.

Accordingly, it is an object of this invention to extract gaseous samples from within a gaseous source and conduct the samples to an analyzer.

Another object is to remove from the gaseous sample to be analyzed undesirable solid particulate contaminants and retain gaseous contaminants such as moisture, carbon dioxide and carbon monoxide.

It is another object of the present invention to preclude the introduction of the particulate matter into the sample gas analyzer by utilizing a filter housing assembly having a filter capable of removing particulate matter from the gas sample in the stack probe.

Yet another object of the present invention resides in a gas sampling assembly that is selectively self-purging of accumulated particulate matter during non-sampling operations.

BRIEF DESCRIPTION OF THE DRAWING

Other objects, advantages, and features of the invention will be more fully appreciated upon consideration of the specification taken in connection with the illustrative drawings in which:

FIG. 1 is a perspective view partly in section of the probe showing the probe extension, filter assembly and eductor assembly.

FIG. 2 is a partial side elevational view of the probe and mounting apparatus.

FIG. 3 is a longitudinal cross-sectional view of the probe and the internal construction thereof.

FIG. 4 is an exploded cross-section fragmentary view of a portion of the probe.

FIG. 5 is a transverse cross-section taken on line 5—5 of FIG. 3.

FIG. 6 is a transverse cross-section taken on line 6—6 of FIG. 3.

FIG. 7 is a rear elevational view of the eductor assembly showing the probe in one mounting configuration on a stack wall.

FIG. 8 is a cross-section view taken on line 8—8 of FIG. 2.

DETAILED DESCRIPTION OF THE DRAWING

Figure 9:
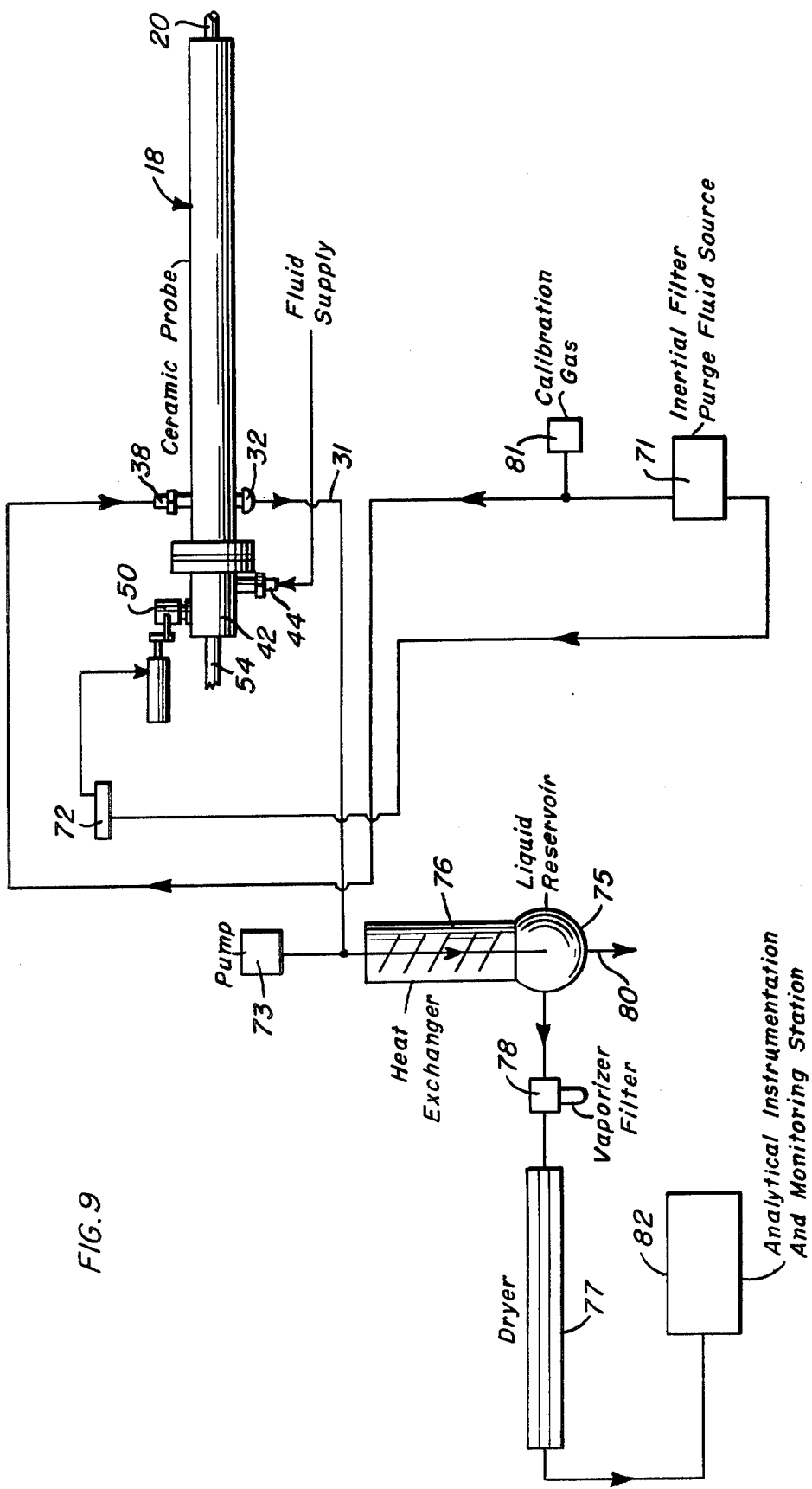
FIG. 9 is a schematic diagram of the conditioning assembly and related apparatus.

Referring to the drawings wherein like numerals indicate like elements in the various figures, FIG. 1 illustrates a preferred embodiment of the filter housing assembly and eductor assembly of the gas sampling extractor. As seen in FIG. 2, a stack wall 10 is provided with an opening 12 around which is mounted the gas sampling extractor mounting flange 13. A flanged elongate tubular inertial filter housing 18 is secured by clamping means 14 to the stack wall 10 and extends through the flange 13 to the interior of the stack.

As shown best in FIG. 1 filter housing 18 has a tubular probe assembly including a coaxial tubular extension 20 terminating in an open end 21 positioned within the stack interior and from which a gas sample may be extracted. As seen in FIG. 3, extension 20 is connected to the filter housing 18 by means of an end coupling 22 having an end portion 29 of reduced diameter mounted within the end 25 of the filter assembly.

End coupling 22 has a recess 28 shown in FIG. 6 for receiving a coupling pin 30 after the extension conduit 20 is connected to the inertial filter housing. Coupling pin 30 is inserted into the coupling pin recess 28 which is offset from the center line of the extension conduit 22 and generally perpendicular to the axis of the tubular coupling. The tubular extension 20 is seated in a counter bore 27 in the end coupling 22 thereby joining the extension 20 to the filter housing 18.

A filtered sample outlet port 32 located adjacent to the filter mounting flange 16 extends through the outer wall 36 of the filter housing 18 and into a filter assembly cell 34. A tubular ceramic filter element 35 constitutes a component of the inertial filter assembly 18 and extends coaxially throughout the length thereof terminating in a shouldered recess 29 in the end coupling 22.

Located in approximate parallel relationship to the sample outlet port 32 and mounted on the outer wall 36 of the inertial filter housing assembly 18 is a calibration inlet port 38, communicating with the cell 34 of the filter assembly 18. The calibration inlet port includes a threaded bushing 39.

An eductor assembly 40 is secured to the filter assembly 18 by a body flange 41 and filter mounting flange 16. Referring now to FIG. 4, an eductor body 42, includes a fluid inlet port 44 in the form of a threaded busing 45 in communication with a chamber 46 defined by an annular space within the eductor body. An eductor jet 48 is positioned partly within said eductor body 40 and extends into said filter housing assembly 18. The eductor jet is initially assembled within an accommodating recess 49 in said eductor body and interconnects the eductor assembly 40 with the interior of the filter housing assembly 18. The eductor jet 48 includes a stepped body portion 33 and an axial passage extending therethrough including first and second diameter portions 51, 53 respectively. The first diameter portion 51 accomodates the innermost end 37 of the concentric filter element 35 providing a receiving recess and support therefor when the eductor assembly 40 is attached to the filter housing assembly 18. In the assembled configuration, as seen in FIG. 3 the reduced portion 56 of the eductor jet extends into chamber 46 and terminates in an end 61 spaced from the base 55 of the eductor venturi 52 and defines a passageway for eductor fluid and gas passing from the filter housing assembly 18 into the eductor assembly 40. A rotatable blowback valve 50 having a passageway 57 therethrough is located between the eductor venturi 52 and the eductor exhaust port 54. A passageway 59 interconnects the eductor venturi 52 to the blowback valve 50. Passageways 57 and 59 in cooperation with eductor exhaust port 54 define when in registry an exhaust passageway for the gas sample and fluid mixture leaving eductor venturi 52.

Interposed between the eductor jet 48 and the filter mounting flange 16 is a compound seal consisting of a flange sealing gasket 64 and a sealing diaphragm 66.

To preclude pressurized fluid, such as steam or air, entering eductor assembly chamber 46 from leaking back across the eductor jet flange 58, sealing diaphragm 66 which may be metallic defines with the eductor body flange a diversionary vent to atmosphere thus precluding contaminating fluids from entering cell 34 of the filter assembly housing and contaminating the stack sample gas therein. The flange sealing gasket 64 on the opposite side of the sealing diaphragm 66 is compressed against the sealing diaphragm 66 between the eductor body flange 41 and the housing mounting flange 16. This arrangement precludes the possibility of eductor fluid contaminating the sample fluid passing through filter element 35 due to leakage from or damage to the ceramic eductor 40.

Blowback valve 50 is rotatably mounted to move selectively between open and closed positions. When closed, the gas or fluid entering chamber 46 flows back through jet 48, inner concentric filter element 35, extension 20 and into the stack interior, thereby purging the filter element 35 of any entrained particulate matter or pollutants that may have accumulated on the inner wall surface. When open, passageway 57 is in registry with eductor exhaust part 54 and passage 59 leading from venturi 52. Fluid introduced into chamber 46 from fluid inlet port 44 is directed into eductor chamber 46 of eductor body 42 and in passing across conical venturi 52 creates a pressure differential thereby drawing a sample of unfiltered gas from within the stack into the inertial filter 35, through eductor jet 48, passageways 59, 57 and exits exhaust vent 54.

OPERATION OF THE GAS SAMPLING EXTRACTOR

The overall operation of the gas sampling extractor will best be understood by reference to FIGS. 3 and 9. In the operation of the gas sampling extractor, three functional modes are contemplated. These are a sampling mode, a purging mode and a calibration mode.

During the sampling mode just described, pressurized fluid is introduced into eductor drive inlet 44, enters chamber 46 thereby creating a pressure drop across the conical venturi 52 of the eductor assembly and exits through the eductor vent 54. The pressure differential draws stack gas into and through extension 20, the ceramic inertial filter 18, eductor assembly 40 and exhausts the sample out through the eductor vent outlet 54. The velocity of sample gas flowing through the extractor and out the eductor exhaust port is at a rate of about two standard cubic feet per minute. If desired, a gas sample to be tested may be extracted through gas outlet 32 from within cell 34 defined by the inner wall of the filter assembly 35 and the outer wall of the filter element 36 by the application of a moderate vacuum applied to sample line 31 by a pump 73. The resulting flow of sample gas within the extractor and line 31 (see FIG. 9) is preferably at a low rate of from about 0.1 liters per minute to about 10 liters per minute. Such a sample gas flow has a negligable effect on the momentum of particles entrained in the stream flowing through the concentric filter element 35, hence the gas sample is substantially free of all particulate matter. Moreover there is little tendency for the particles to enter and become entrapped within the pores of the inner filter wall of filter element 35 because of the low velocity of the withdrawn sample. Any particles adhering momentarily to the inner surface of the concentric wall of filter element 35 are flushed away by the high velocity of the stack gas stream flowing through the inertial filter element 35.

The filtered gas sample containing acid mist and water vapor is conducted to a heat exchanger 76, as seen schematically in FIG. 9 which utilizes air as a cooling medium. The cooling air flow is countercurrent to the sample flow and gains heat from the gas sample as it passes through the heat exchanger. As the sample gas cools in the heat exchanger, any condensibles or entrained liquids are condensed and collected in a liquid reservoir 75 at the bottom of the heat exchanger. The stack gas sample is then conducted from the upper portion of the liquid reservoir into a vaporizer/filter 78, located at the outlet of the heat exchanger. The vaporizer/filter is heated to approximately 120 degrees C. The vaporizer aids dryer 77 is removing liquids by vaporizing the majority of entrained liquids in the sample gas. Thereafter the dry, filtered gas sample is conducted to a remote monitering station 82 for analysis.

When it is desirable or there is an indication, such as a pressure drop in the system, that filter 35 is to be purged of any entrained particulate matter, blowback valve 50 is moved to the closed position. Pressure fluid such as air or steam is then directed from a fluid source 71 through a valve 72, the eductor assembly 40 and back through the filter 35 thus flusing any particulate material which may have been retained on the interior walls of the inertial filter 35 back into the stack stream. During the purging mode the liquid reservoir 75 on the heat exchanger is simultaneously drained through drain 80.

During the calibration mode the gas driven eductor is closed and a calibration gas 81 may then be supplied through the calibration port manually, by an operator, or automatically, by an automatic calibration assembly. Supplying calibration gas in this manner allows the calibration gas to flow through all sampling components. By introducing the calibration gas directly to the sampling system and then to the analysis system, sample loss may be calculated.

Obvious modifications and variations of the present invention are possible in light of the foregoing teachings without departing from the spirit and scope of the appended claims.

What is claimed:

1. A gas sampling extractor for extracting a gas sample from a gaseous source for analysis comprising an elongate tubular filter housing having a flanged end and an oppositely disposed terminal end portion, said filter housing including a tubular probe assembly and a coaxial tubular extension mounted on said terminal end of said housing; a tubular ceramic filter element coaxially mounted within said housing coextensively therewith and dimensioned to define a cell therebetween, an eductor including an eductor body having a flange connected to the opposite flanged end of said filter housing; valve means in said eductor body moveable between first and second controlling positions, and a compound seal interposed between said filter housing and said eductor, said compound seal including a non-metallic gasket which contacts the housing flange and a flexible metallic diaphragm which contacts the eductor body flange.

2. A gas sampling extractor for extracting a gas sample from a gaseous source for analysis comprising an elongate tubular filter housing having a flanged end and an oppositely disposed terminal end portion, said filter housing including a tubular probe assembly and a coaxial tubular extension mounted on said terminal end of said housing to extract a gas sample from said source and conduct said sample into said filter housing; a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port in said housing and communicating with said cell; means for selectively introducing a calibration gas into and for withdrawing said gas from the interior of said cell; an eductor including a flanged eductor body mounted on the flanged end of said housing, means defining a chamber within said eductor body for receiving eductor fluid, an eductor fluid inlet extending into said eductor body and in communication with said chamber for introducing eductor fluid therein, an eductor outlet in said body in communication with said valve for discharging eductor fluid and sample gas from said eductor, a shouldered eductor jet extending at least partially into said eductor body and positioned between said ceramic filter element and partially within said chamber, said shouldered eductor jet having a stepped body portion including first and second diameter portions, said first diameter portion providing a recess for receiving and supporting said filter element, and said second diameter portion having a reduced portion extending into and seated within said eductor thereby interconnecting said eductor and said filter housing and defining a coaxial passage therethrough for said gas sample passing from said filter element into said eductor, an eductor venturi in said eductor body adjacent said chamber and extending coaxially from said chamber, valve means in said eductor body between said inlet and said outlet and moveable between first and second controlling positions whereby eductor fluid directed into said inlet and said chamber may be selectively conducted to said outlet and said filter element, and a compound seal interposed between said housing portion and said eductor portion including a flange sealing gasket and a sealing diaphragm.

3. A gas sampling extractor for extracting a gas sample from a gaseous source for analysis comprising an elongate tubular filter housing having a flanged end and an oppositely disposed terminal end portion, said filter housing including a tubular probe assembly and a coaxial tubular extension mounted on said terminal end of said housing to extract a gas sample from said source and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port in said housing and communicating with said cell, means for selectively introducing a calibration gas into and for withdrawing said gas from the interior of said cell, an eductor including a flanged eductor body mounted on the flanged end of said housing, a valve mounted on and extending into said eductor body, a chamber within said eductor body, an eductor fluid inlet extending into said eductor body and in communication with said chamber for conducting eductor fluid into said chamber, a passage within said eductor body in communication with said chamber and said valve, an eductor fluid outlet in said body in communication with said valve for discharging eductor fluid and sample gas from said eductor, a shouldered eductor jet extending at least partially into said eductor body and positioned between said ceramic filter element and partially within said chamber, an eductor venturi in said eductor body adjacent to and in indirect communication with said chamber and said passage and extending coaxially outwardly therefrom; said valve in said eductor body positioned between said venturi and said eductor outlet and having a passage therethrough and moveable between first and second controlling positions whereby eductor fluid directed into said inlet and said chamber may be selectively conducted to said outlet and said filter element, and a compound seal interposed between said housing portion and said eductor portion including a non-metallic flange sealing gasket and a flexible metallic sealing diaphragm positioned between said eductor body flange and said filter housing flange respectively, said gasket positioned adjacent said filter housing flange and said diaphragm positioned adjacent said eductor body flange, said compound seal defining a diversionary vent to atmosphere thereby preventing eductor fluid within said eductor chamber from passing around said shouldered eductor jet and entering said filter housing cell and contaminating said stack sample gas therein.

4. A gas sampling extractor for extracting a gas sample from a gaseous source for analysis comprising an elongate tubular filter housing having a flanged end and an oppositely disposed terminal end portion, a flanged eductor connector to said filter housing, a compound seal interposed between said housing flange and said eductor flange including a non-metallic flange sealing gasket contacting said housing flange and a flexible metallic sealing diaphragm contacting said eductor flange, said filter housing including a tubular probe assembly and a coaxial tubular extension mounted on said terminal end of said housing to extract a gas sample from said source and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port mounted on said filter housing and communicating with said cell, means for selectively introducing a calibration gas into and for withdrawing said gas from the interior of said cell, said eductor including a flanged eductor body connected to said filter housing portion of said extractor, an inlet in said eductor body for introducing eductor fluid into said eductor, an eductor outlet for eductor fluid and sample gas, a chamber within said body connected to said inlet to receive said eductor fluid, a shouldered eductor jet extending at least partially into said eductor body and positioned between said ceramic filter and partially within said chamber, an eductor venturi in said eductor body adjacent to and in indirect communication with said chamber and extending coaxially outwardly therefrom, and a valve mounted on and extending into said eductor body positioned between said venturi and said eductor inlet and outlet having a passage therethrough in communication with said venturi and moveable between first and second controlling positions whereby eductor fluid directed into said inlet and said chamber may be selectively conducted to said outlet and said filter element, said first controlling position of said valve interconnecting said inlet and said outlet, whereby said fluid passing through said eductor chamber, eductor venturi jet and said outlet induces a partial vacuum in said eductor and draws a gas sample from said source through said terminal end portion and ceramic filter element of said filter housing, for analysis thereof, and second controlling position of said valve closes said outlet and directs said eductor fluid into said filter housing element and terminal end portion mounted thereon, and into said gaseous source thereby purging said filter element of accumulated pollutants.

5. A gas sampling extractor for extracting a gas sample from a stack for analysis including an elongate tubular filter housing having a flanged end and an oppositely disposed terminal end portion, a flanged eductor connected to said filter housing, a compound seal interposed between said housing and said eductor including a non-metallic flange sealing gasket contacting said housing flange and a flexible metallic sealing diaphragm contacting said eductor flange, said filter housing including a tubular probe assembly and a coaxial tubular extension mounted on said terminal end of said housing to extract a gas sample from the interior of said stack and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, means for selectively introducing a calibration gas into and for withdrawing said gas from the interior of said cell, said eductor including a flanged eductor body connected to said filter housing of said extractor, an inlet in said eductor body for introducing eductor fluid into said eductor, an eductor outlet in said eductor body for eductor fluid and sample gas, a chamber within said eductor body connected to said inlet to receive said eductor fluid, a shouldered eductor jet extending at least partially into said eductor body and positioned between said ceramic filter and partially within said chamber, an eductor venturi in said eductor body adjacent to and in indirect communication with said chamber and extending coaxially outwardly therefrom, and a valve mounted on and extending into said eductor body between said venturi and said eductor outlet, and said valve being moveable between first and second controlling positions whereby eductor fluid directed into said inlet and said chamber may be selectively conducted to said outlet and said filter element, said first controlling position of said valve directing eductor fluid to said eductor outlet, whereby it induces a partial vacuum in said eductor venturi and draw a gas sample from said source through said terminal end portion and ceramic filter element of said filter housing, said second controlling position of said valve closing said outlet and directing said eductor fluid through said eductor, said filter housing element and terminal end portion mounted thereon, and into said gaseous source thereby purging said filter element of accumulated pollutants.

6. A gas sampling extractor for extracting a gas sample from a stack for analysis including an elongate tubular filter housing having a flanged end and an oppositely disposed terminal end portion, a flanged eductor connected to said filter housing, a compound seal interposed between said housing and said eductor including a non-metallic flange sealing gasket contacting said housing flange and a flexible metallic sealing diaphragm contacting said eductor flange, said filter housing including a tubular probe assembly and a coaxial tubular extension mounted on said terminal end of said housing to extract a gas sample from the interior of said stack and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port mounted on said filter housing and communicating with said cell, means for selectively introducing a calibration gas into and for withdrawing said gas from the interior of said cell, said eductor including a flanged eductor body connected to said filter housing of said extractor, and inlet in said eductor body for introducing eductor fluid into said eductor, an eductor outlet for eductor fluid and sample gas, a chamber within said body connected to said inlet to receive said eductor fluid, a shouldered eductor jet extending at least partially into said eductor body and positioned between said ceramic filter and partially within said chamber, an eductor venturi in said eductor body adjacent to and in indirect communication with said chamber and extending coaxially outwardly therefrom, a valve mounted on and extending into said eductor body positioned between said venturi and said eductor inlet and said outlet having a passage therethrough in communication with said venturi and moveable between first and second controlling positions whereby eductor fluid directed into said inlet and said chamber may be selectively conducted to said outlet and said filter element, and said flanged sealing gasket and said sealing diaphragm of said compound seal constitutes a compound element defining a diversionary vent to atmosphere thereby preventing eductor fluid within said eductor chamber from passing around said shouldered eductor jet and entering said filter housing cell and comtaminating said stack sample gas therein.

7. A gas sampling extractor for extracting from a stack a stack gas sample for analysis including conditioning and analytical apparatus mounted exteriorly of said stack and communicating with said extractor, an elongate tubular filter housing having a flanged end and an oppositely disposed terminal end portion, a flanged eductor connected to said filter housing and mounted exteriorly of said stack, a compound seal interposed between said housing and said eductor including a non-metallic flange sealing gasket contacting said housing flange and a flexible metallic sealing diaphragm contacting said eductor flange, said filter housing including a tubular probe assembly and a coaxial tubular extension mounted on said terminal end of said housing to extract a stack gas sample from the interior of said stack and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port mounted on said filter housing and communicating with said cell, means for selectively introducing a calibration gas into and for withdrawing said gas from the interior of said cell, said eductor including a flanged eductor body connected to said filter housing of said extractor, an inlet in said eductor body for introducing eductor fluid into said eductor, an eductor outlet for eductor fluid and sample gas, a chamber within said eductor body connected to said inlet to receive said eductor fluid, a shouldered eductor jet extending at least partially into said body and positioned between said ceramic filter and partially within said chamber, an eductor venturi in said eductor body adjacent to and in indirect communication with said chamber and extending coaxially outwardly therefrom, valve means mounted on and extending into said eductor body positioned between said venturi and said eductor inlet and said outlet having a passage therethrough in communication with said venturi and moveable between first and second controlling positions whereby eductor fluid directed into said inlet and said chamber may be selectively conducted to said outlet thereby inducing a partial vacuum in said chamber whereby said eductor fluid and gas sample in said chamber passes through said venturi and said valve and exits said eductor body through said eductor outlet, and said conditioning apparatus includes a sample line connected to said sample outlet, a vacuum pump connected to said sample line, a heat exchanger connected to said vacuum pump and said sample line, a vaporizer filter connected to said heat exchanger and said sample line, a dryer connected to said vaporizer filter and said sample line, analytical apparatus connected to said dryer and said sample line for receiving said sample, and means for extracting a gas sample from said cell through said sample gas outlet and conducting said gas sample to said heat exchanger, said vaporizer filter and said dryer to remove condensibles and entrained liquids within said gas sample and thereafter conducting said dry, filtered gas sample to said analytical apparatus.

8. A gas sampling extractor for extracting from a stack a stack gas sample for analysis including conditioning and analytical apparatus mounted exteriorly of said stack and communicating with said extractor, an elongate tubular filter housing having a flanged end and an oppositely disposed terminal end portion, a flanged eductor mounted exteriorly of said filter stack, a compound seal interposed between said filter housing and said eductor including a non-metallic flange sealing gasket contacting said housing flange and a flexible metallic sealing diaphragm contacting said eductor flange, said filter housing including a tubular probe assembly and a coaxial tubular extension mounted on said terminal end of said housing to extract a stack gas sample from the interior of said stack and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port mounted on said filter housing and communicating with said cell, means for selectively introducing a calibration gas into and for withdrawing said gas from the interior of said cell, said eductor including a flanged eductor body connected to said filter housing of said extractor, an inlet in said eductor body for introducing eductor fluid into said eductor, an eductor outlet for eductor fluid and sample gas, a chamber within said eductor body connected to said inlet to receive said eductor fluid, a shouldered eductor jet extending at least partially into said body and positioned between said ceramic filter and partially within said chamber, an eductor venturi in said eductor body adjacent to and in indirect communication with said chamber and extending coaxially outwardly from said chamber, valve means mounted and extending into said eductor body positioned between said venturi and said eductor inlet and said outlet having a passage therethrough in communication with said venturi and moveable between first and second controlling positions whereby eductor fluid directed into said inlet and said chamber may be selectively conducted to said outlet thereby inducing a partial vacuum in said chamber whereby said eductor fluid and gas sample in said chamber passes through said venturi and said valve and exits said eductor body through said eductor outlet, and said coaxial tubular extension includes an end coupling having an end portion of reduced diameter mounted within the end of said terminal end portion of said filter housing, a counter bore within said end portion of said filter housing for receiving said tubular extension, a coupling pin recess within said end coupling, said coupling pin recess being offset from the center line of said tubular extension and generally perpendicular to the axis of said end portion, said tubular extension being seated in said counter bore, and said coupling pin being inserted into said coupling pin recess thereby joining said tubular extension to said filter housing.

9. A gas sampling extractor for extracting a gas sample from a stack for analysis comprising an elongate tubular filter housing having a flanged end and an oppositely disposed terminal end portion, said filter housing including a tubular probe assembly and a coaxial tubular extension mounted on said terminal end of said housing to extract a gas sample from said stack and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port in said housing and communicating with said cell; means for selectively introducing a calibration gas into and for withdrawing said gas from the interior of said cell, an eductor including a flanged eductor body mounted on the flanged end of said housing, a valve mounted on and extending into said eductor body, a chamber within said eductor body for receiving eductor fluid, an eductor fluid inlet extending into said eductor body and in communication with said chamber for introducing eductor fluid therein, an eductor outlet in said body in communication with said valve for discharging eductor fluid and sample gas from said eductor, a shouldered eductor jet extending at least partially into said eductor body and positioned between said ceramic filter element and partially within said chamber, an eductor venturi in said eductor body adjacent said chamber and extending coaxially from said chamber, said valve extending into said eductor body positioned between said inlet and said outlet and moveable between first and second controlling positions whereby eductor fluid directed into said inlet and said chamber may be selectively conducted to said outlet and said filter element, a compound seal interposed between said flanged housing portion and said flanged eductor portion including a non-metallic flange sealing gasket contacting said housing flange and a flexible metallic sealing diaphragm contacting said eductor flange, and said shouldered eductor jet having a stepped body portion including first and second diameter portions, said first diameter portion providing a recess for receiving and supporting said filter element, and said second diameter portion having a reduced portion extending into and sealed within said eductor thereby interconnecting said eductor and said filter housing and defining a coaxial passage therethrough for said gas sample passing from said filter element into said eductor.

10. A gas sampling extractor for extracting a gas sample from a gaseous source for analysis including conditioning and analytical apparatus communicating with said extractor, an elongate tubular filter housing having a flanged end and an oppositely disposed terminal end portion, a flanged eductor connected to said filter housing, a compound seal interposed between said housing and said eductor including a non-metallic flange sealing gasket contacting said housing flange and a flexible metallic sealing diaphragm, contacting said eductor flange, said filter housing including a tubular probe assembly and a coaxial tubular extension mounted on said terminal end of said housing to extract a gas sample from said source and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port mounted on said filter housing and communicating with said cell, means for selectively introducing a calibration gas into and for withdrawing said gas from the interior of said cell, said eductor including a flanged eductor body connected to said filter housing of said extractor, an inlet in said eductor body for introducing eductor fluid into said eductor, an eductor outlet for eductor fluid and sample gas, a chamber within said eductor body connected to said inlet to receive said eductor fluid, a shouldered eductor jet extending at least partially into said body and positioned between said ceramic filter and partially within said chamber, an eductor venturi in said eductor body adjacent to and in indirect communication with said chamber and extending coaxially outwardly therefrom, valve means mounted on and extending into said eductor body positioned between said venturi and said eductor inlet and said outlet having a passage therethrough in communication with said venturi and moveable between first and second controlling positions whereby eductor fluid directed into said inlet and said chamber may be selectively conducted to said outlet thereby inducing a partial vacuum in said chamber whereby said eductor fluid and gas sample in said chamber passes through said venturi and said valve and exits said eductor body through said eductor outlet, and said conditioning apparatus includes a sample line connected to said sample outlet, a vacuum pump connected to said sample line, a heat exchanger connected to said vacuum pump and said sample line, a vaporized filter connected to said heat exchanger and said sample line, a dryer connected to said vaporizer filter and said sample line, analytical apparatus connected to said dryer and said sample line for receiving said sample, and means for extracting a gas sample from said cell through said sample gas outlet and conducting said gas sample to said heat exchanger, said vaporizer filter and said dryer to remove condensibles and entrained liquids within said gas sample and thereafter conducting said dry, filtered gas sample to said analytical apparatus.

11. A gas sampling extractor for extracting a gas sample from a gaseous source for analysis including conditioning and analytical apparatus communicating with said extractor, an elongate tubular filter housing having a flanged end and an oppositely disposed terminal end portion, a flanged eductor connected to said filter housing, a compound seal interposed between said filter housing and said eductor including a non-metallic flange sealing gasket contacting said housing flange and a flexible metallic sealing diaphragm contacting said eductor flange, said filter housing including a tubular probe assembly and a coaxial tubular extension mounted on said terminal end of said housing to extract a gas sample from the gaseous source and conduct said sample into said filter housing, a tubular ceramic filter element coaxially mounted within said housing coextensively therewith and dimensioned to define a cell therebetween extending substantially the length of said housing and said filter element and in communication with said tubular extension, a sample extraction port mounted on said filter housing and in communication with said cell, a gas calibration port mounted on said filter housing and communicating with said cell, means for selectively introducing a calibration gas into and for withdrawing said gas from the interior of said cell, said eductor including a flanged eductor body connected to said filter housing of said extractor, an inlet in said eductor body for introducing eductor fluid into said eductor, an eductor outlet for eductor fluid and sample gas, a chamber within said eductor body connected to said inlet to receive said eductor fluid, a shouldered eductor jet extending at least partially into said body and positioned between said ceramic filter and partially within said chamber, an eductor venturi in said eductor body adjacent to and in indirect communication with said chamber and extending coaxially outwardly from said chamber, valve means mounted on and extending into said eductor body positioned between said venturi and said eductor inlet and said outlet having a passage therethrough in communication with said venturi and moveable between first and second controlling positions whereby eductor fluid directed into said inlet and said chamber may be selectively conducted to said outlet thereby inducing a partial vacuum in said chamber whereby said eductor fluid and gas sample in said chamber passes through said venturi and said valve and exits said eductor body through said eductor outlet, and said coaxial tubular extension includes an end coupling having an end portion of reduced diameter mounted within the end of said terminal end portion of said filter housing, a counter bore within said end portion of said filter housing for receiving said tubular extension, a coupling pin recess within said end coupling, said coupling pin recess being offset from the center line of said tubular extension and generally perpendicular to the axis of said end portion, said tubular extension being seated in said counter bore, and said coupling pin being inserted into said coupling pin recess thereby joining said tubular extension to said filter housing for further analysis thereof.

12. A gas sampling extractor as claimed in claim 1 wherein said tubular filter housing, terminal end portion, coaxial tubular extension, tubular filter element, eductor and valve means are porous ceramic alumina.

13. A gas sampling extractor as claimed in claim 1 wherein said compound seal consists of a synthetic polymeric gasket and a flexible metallic diaphragm.

14. A gas sampling extractor as claimed in claim 1 wherein said filter housing, terminal end portion, coaxial tubular extension and eductor body are made of metallic material.

15. A gas sampling extractor as claimed in claim 1 wherein the porosity of said tubular ceramic filter element is not less than about 5 microns.

16. A gas sampling extractor as claimed in claim 1 wherein said eductor establishes a flow of sample gas through said tubular ceramic filter element of about two standard cubic feet per minute.

17. A gas sampling extractor as claimed in claim 2 wherein said eductor establishes a flow of sample gas through said tubular ceramic filter element of about two standard cubic feet per minute.

18. A gas sampling extractor as claimed in claim 2 wherein the porosity of said tubular ceramic filter element is not less than about 5 microns.

19. A gas sampling extractor as claimed in claim 3 wherein the compound seal flange sealing gasket is a synthetic polymeric gasket.

20. A gas sampling extractor as claimed in claim 4 wherein the valve is a rotary plug valve.

21. A gas sampling extractor as claimed in claim 5 wherein the valve is a rotary plug valve.

22. A gas sampling extractor as claimed in claim 6 wherein the compound seal flange sealing gasket is a synthetic polymeric gasket.

23. A gas sampling extractor as claimed in claim 8 wherein the coaxial tubular extension is a porous alumina ceramic tubular extension.

24. A gas sampling extractor as claimed in claim 8 wherein the coaxial tubular extension is a non-metallic tubular extension.

25. A gas sampling extractor as claimed in claim 8 wherein the coaxial tubular extension is a metallic tubular extension.

26. A gas sampling extractor as claimed in claim 9 wherein said eductor establishes a flow of sample gas through said tubular ceramic filter element of from about two standard cubic feet per minute.

27. A gas sampling extractor as claimed in claim 9 wherein the porosity of said tubular ceramic filter element is not less than about 5 microns.

28. A gas sampling extractor as claimed in claim 2, 7 or 9 wherein sample gas is extracted through said sample extraction port at a flow rate of from about 0.1 liters to about 10 liters per minute.

* * * * *